United States Patent [19]

Bourland et al.

[11] Patent Number: 4,827,763
[45] Date of Patent: May 9, 1989

[54] PRESSURE MAPPING SYSTEM WITH CAPACITIVE MEASURING PAD

[75] Inventors: Joe D. Bourland; Charles F. Babbs; Leslie A. Geddes; Willis A. Tacker, Jr.; George P. Graber, all of W. Lafayette, Ind.

[73] Assignee: Purdue Research Foundation, West Lafayette, Ind.

[21] Appl. No.: 850,518

[22] Filed: Apr. 11, 1986

[51] Int. Cl.$^4$ .............................................. A61B 5/10
[52] U.S. Cl. ................................. 73/172; 73/862.04; 361/283; 128/722
[58] Field of Search .......................... 73/172, 862.04; 340/626; 361/283; 128/722, 779

[56] References Cited

U.S. PATENT DOCUMENTS

| | | | |
|---|---|---|---|
| 3,818,756 | 6/1974 | Barron et al. | 73/172 |
| 3,926,177 | 12/1975 | Hardway, Jr. et al. | 128/722 |
| 4,134,063 | 1/1979 | Nicol et al. | 324/61 R |
| 4,136,682 | 1/1979 | Pedotti | 73/172 |
| 4,266,263 | 5/1981 | Haberl et al. | 361/283 |
| 4,267,728 | 5/1981 | Manley et al. | 73/172 |
| 4,381,788 | 5/1983 | Douglas | 361/283 |
| 4,437,138 | 3/1984 | Nicol | 361/283 |
| 4,526,043 | 7/1985 | Boie et al. | 361/283 |
| 4,581,677 | 4/1986 | Hruby et al. | 361/283 |
| 4,600,016 | 7/1986 | Boyd et al. | 128/779 |
| 4,644,801 | 2/1987 | Kustanovich | 73/172 |

FOREIGN PATENT DOCUMENTS

| | | | |
|---|---|---|---|
| 2653556 | 6/1977 | Fed. Rep. of Germany | 73/172 |
| 2071852 | 9/1981 | United Kingdom | 324/61 P |

Primary Examiner—William A. Cuchlinski, Jr.
Assistant Examiner—Thomas B. Will
Attorney, Agent, or Firm—Burns, Doane, Swecker & Mathis

[57] ABSTRACT

A pressure distribution measuring system includes a pad of insulating material disposed between two linear arrays of electrodes to form a matrix of capacitive nodes. A capacitance related output signal that is obtained from a node of interest is used as a feedback signal and applied to other capacitors that are connected in common with the node of interest. The feedback signal inhibits the flow of current through these commonly connected capacitors, and thereby isolates the measured signal from any changes in the capacitance of these other capacitors. The pad includes a cental array of linear electrodes sandwiched between two layers of dielectric foam material. Two outer, aligned linear electrode arrays, oriented perpendicular to the central array, are respectively disposed on the outside surfaces of the dielectric layers. In a preferred form, alternating electrodes in each outer array are located on opposite sides of a support substrate. This construction increases the amplitude of the measured signal, isolates the measured signal from the ambient environment, and reduces the susceptibility of the measuring process to errors caused by wrinkling of the pad as a person lies on it, or the like.

13 Claims, 6 Drawing Sheets 4,827,763

PRESSURE MAPPING SYSTEM WITH CAPACITIVE MEASURING PAD

BACKGROUND OF THE INVENTION

The present invention is directed to a system for detecting and measuring pressure distribution, and more particularly to a system which employs a pad to provide a qualitative indication of pressure distribution on a surface.

Pressure sensing pads are known for use in applications such as the detection of apnea or the like. They can be placed on the crib of an infant and are used to detect regular and periodic changes in pressure occasioned by the respiration and movement of the infant. If the infant should stop breathing, the failure to detect a change in pressure for a predetermined period of time provides an early indication of a possible alarm condition.

While most pressure sensing pads of the type known heretofore are capable of detecting the interruption of respiration, they are not suited for other uses. In particular, it is desirable to be able to measure the distribution of pressure on a surface. Information of this type would be invaluable to designers of sleep surfaces and furniture, for example. By knowing where the high-pressure points of a prone person are located, a bed can be designed which will more evenly distribute pressure and thereby diminish the occurrence of bedsores on patients who are confined for long periods of time. Similarly, the design of ergonomically efficient furniture is facilitated with such information.

Apnea monitoring pads are not suited for these types of application because they are essentially qualitative measuring devices. In other words, they can detect if a pressure is being applied and whether it is changing, but they do not indicate how much pressure is being applied. Further they do not have the ability to provide any spatial resolution to the sensed pressure; they merely detect that it exists somewhere on the surface of the pad.

A significant problem that is encountered when attempts are made to provide spatial resolution of an applied pressure is the effect which various measuring points have on one another. For example, U.S. Pat. Nos. 4,134,063 and 4,437,138 disclose a pressure sensing mat that comprises a matrix of capacitive elements. Each capacitive element defines a measuring point. When a measurement is to be taken at a particular point, a voltage signal is applied to one terminal of the capacitor at that point, and a signal is obtained at the other terminal which is indicative of capacitance. Since the capacitance varies with the pressure on the mat at the location of the capacitor, the obtained signal provides pressure related information.

However, since all of the capacitors are connected to each other in the matrix arrangement, errors can occur in the pressure measurement. More particularly, the obtained signal will be influenced not only by the capacitance at the measuring point of interest but also by the capacitances of the surrounding points. Thus, changes in the surrounding pressures will be indicated in the measured signal and could result in erroneous readings.

The previously noted '063 patent contains a recognition of this problem. As a solution, it proposes that each of the input lines that supplies the voltage signal to the capacitors be connected to ground by a low-ohmic resistor. Apparently the resistor functions to shunt some of the error signal away from the output terminal of the capacitor of interest. While this approach attenuates the effect of the error on the measured signal, it would be preferable to eliminate or compensate the error signal to the greatest extent that can be practically obtained.

Accordingly, it is a general object of the present invention to provide a novel capacitive system for measuring the spatial distribution of pressure.

It is a more specific object along these lines to provide such a system which eliminates the errors occasioned by interaction among commonly connected capacitors.

It is a further object of the invention to provide a novel pad structure for providing capacitive type measurements.

BRIEF STATEMENT OF THE INVENTION

In accordance with the present invention, these objects and their attendant advantages are provided in a pressure distribution measuring system that comprises a pad of insulating material disposed between two linear arrays of electrodes to form a matrix of capacitive nodes. A capacitance related output signal that is obtained from a node of interest is used as a feedback signal and applied to other capacitors that are connected in common with the node of interest. The feedback signal inhibits the flow of current through these commonly connected capacitors, and thereby isolates the measured signal from any changes in the capacitance of these other capacitors.

As a further feature of the invention, a novel pad construction is proposed which increases the amplitude of the measured signal, isolates the measured signal from the ambient environment, and reduces the susceptibility of the measuring process to errors caused by wrinkling of the pad as a person lies on it, or the like.

The manner in which these concepts are implemented is explained in greater detail hereinafter with reference to a preferred embodiment of the invention illustrated in the accompanying drawings.

BRIEF DESCRIPTION OF THE DRAWING

FIG. 8 is a cross-sectional view of an alternative type of dielectric layer for the pad.

DESCRIPTION OF THE ILLUSTRATED EMBODIMENT

In the following description, particular reference is made to the use of the invention in the context of measuring the distribution of the pressure exerted by a person lying on a mattress. It will be appreciated, however, that the practical applications of the invention extend to many other areas in which knowledge of actual pressure and/or its distribution would be useful.

Figure 1:
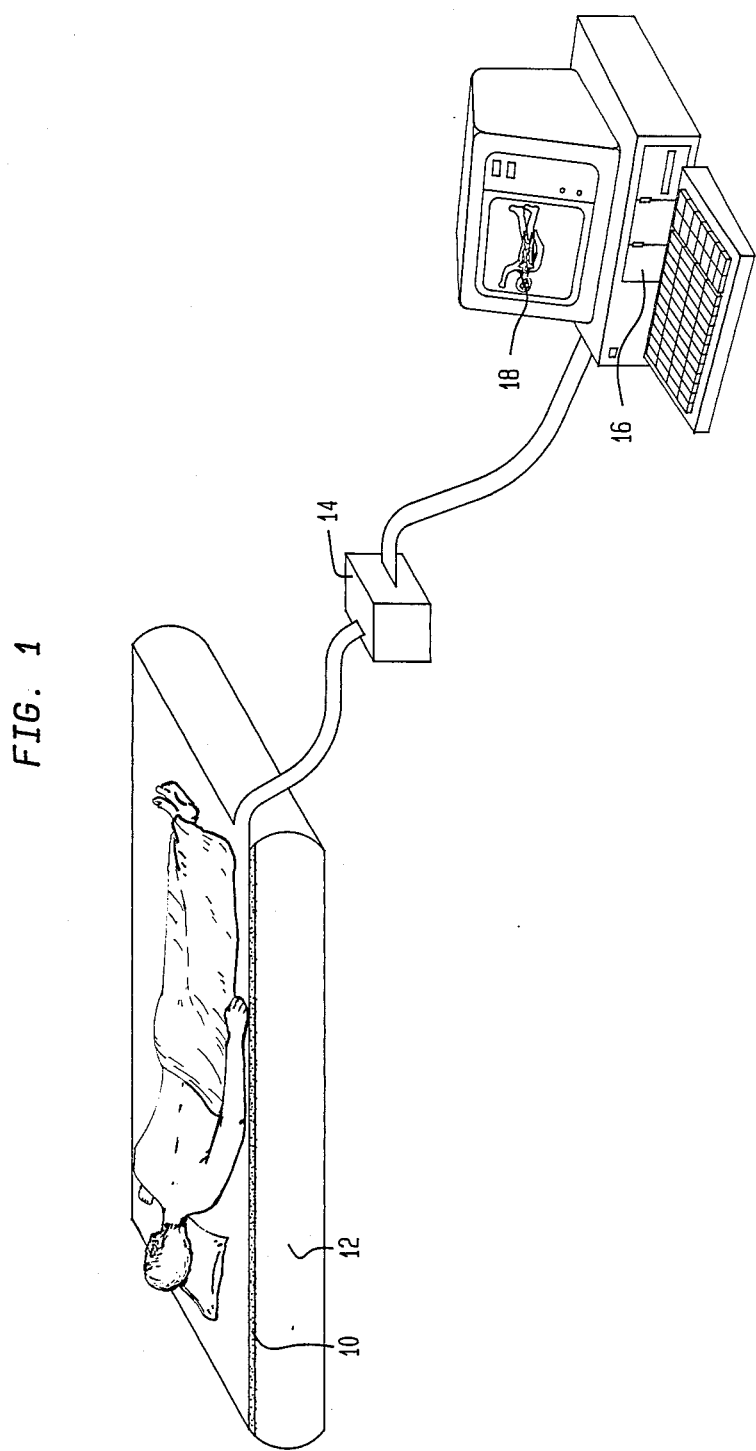
FIG. 1 is a general perspective view of the overall measuring system as it might be used to determine the distribution of pressure of a person lying on a mattress.

Referring to FIG. 1, the pressure measuring system of the present invention is comprised of three main components, a pressure sensitive pad 10 that can be placed on top of a mattress 12 to measure the weight distribution of a person lying on it, an interface unit 14 for supplying electrical driving signals to the pad and receiving pressure sensitive output signals from it, and a computer 16 with an associated graphic display monitor 18 for controlling the interface unit and processing the output signals from the pad. In operation, the pad 10 produces output signals that are indicative of the pressure that is sensed at each of a multiplicity of points over its surface area. The computer 16 receives these signals, by way of the interface unit, and causes a display to be generated which illustrates the distribution of the weight of the patient over the area of the pad.

Figure 2:
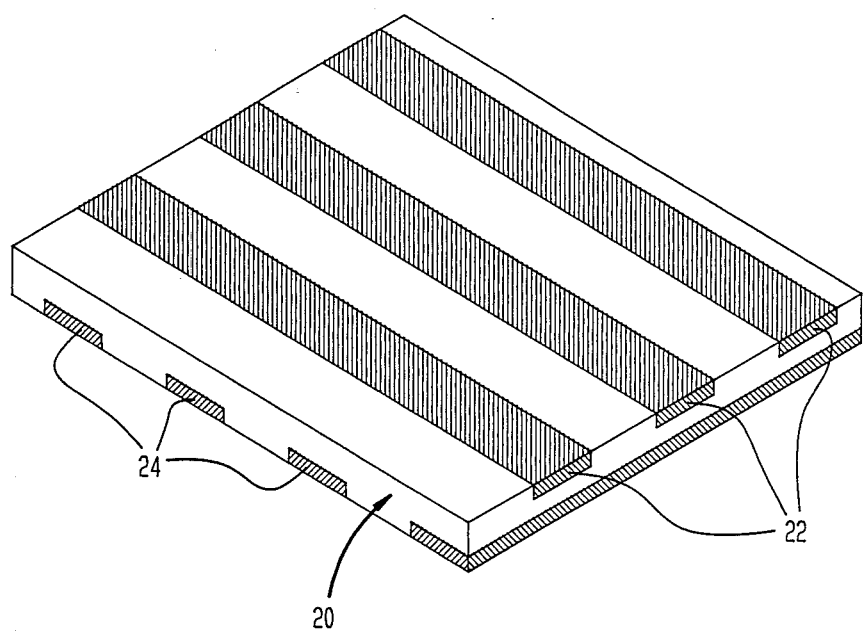
FIG. 2 is a perspective view illustrating the general construction of a pressure-responsive capacitive measuring pad.

The basic construction of the pad 10 is illustrated in FIG. 2. It comprises a compressible dielectric layer 20 having two linear arrays of electrodes 22 and 24 respectively disposed on opposite sides thereof. The dielectric layer can be an open cell foam having a nominal, i.e., unloaded, thickness of about 5 mm. One of the arrays 22 comprises a series of parallel linear electrodes that are oriented in one direction. The other array 24 similarly comprises a series of parallel linear electrodes which are oriented in a direction that is perpendicular to the orientation of the electrodes in the first array 22. Each intersection of an electrode of one array with an electrode of the other array defines a measuring node. Since the thickness of the dielectric layer 20 between the intersecting electrodes varies with applied pressure, its capacitance also varies. Thus the capacitance at each node provides an indication of the pressure applied at that point.

Figure 3:
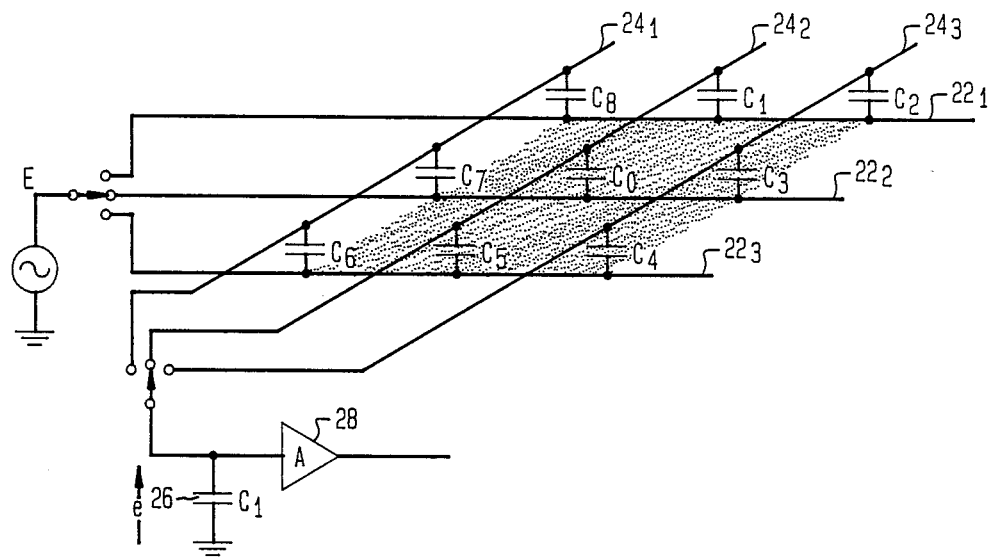
FIG. 3 is a schematic diagram of the capacitive circuit formed by the pad of FIG. 2.

The equivalent circuit that is formed by the structure of FIG. 2 is illustrated in FIG. 3. The measuring nodes are represented by capacitors $C_0$–$C_8$ that are disposed in a matrix arrangement. All of the capacitors in a row of the matrix are connected in common to one of the electrodes 22 of the first array, and all capacitors in a column of the matrix are connected in common to one of the electrodes 24 of the other array. When it is desired to measure the capacitance of a particular node, a driving signal having a known voltage E is applied to the electrode 22 associated with the row in which the node is located. Referring to the specific example illustrated in FIG. 3, if it is desired to measure the capacitance of capacitor $C_0$, the driving signal is applied to the middle electrode $22_2$. The measured capacitance is sensed on the electrode $24_2$ associated with the column in which the capacitor is located. This electrode is connected to a fixed capacitor 26 having a value $C_i$ which is much greater than the individual capacitance of the variable capacitors $C_0$–$C_8$. For example, the capacitance $C_i$ can be 3-4 times greater than the maximum capacitance at the individual measuring nodes. The junction of the measured and fixed capacitors is connected to an amplifier 28 which produces an output signal related to the capacitance of the node $C_0$ according to the following relationship:

$$e = \frac{C_o}{C_o + C_i} E$$

where
 e is the voltage across the fixed capacitor 26,
 E is the voltage that is applied as a driving signal,
 $C_i$ is the capacitance of the fixed capacitor 26, and
 $C_o$ is the variable capacitance at the measuring node.

The capacitance at the node is determined by the thickness of the dielectric layer at that point, which in turn is a function of pressure. A higher capacitance represents a thinner dielectric layer and hence a greater applied pressure. The transfer function of the system can be defined in terms of pressure as follows:

$$\frac{e}{E} = K_0 \frac{1 + K_1 p}{1 + K_2 p}$$

where
 $K_0$, $K_1$ and $K_2$ are constants related to the stress - strain characteristics of the dielectric layer, the square area of a node, the capacitance $C_i$ and other circuit parameters, and
 p is pressure applied at the node.

Thus, the signal that is obtained on the electrode 24 can be quantified in terms of applied pressure as follows:

$$p = \frac{K_0 E - e}{e K_2 - K_0 K_1 E}$$

One factor that needs to be addressed when pressure is to be quantified is the interaction among the nodes. In particular, the signal which is sensed on the electrode $24_2$ will not be limited to only the capacitance at the node $C_o$. Referring to FIG. 3, the primary path from the driving electrode $22_2$ to the sensing electrode $24_2$ is through the capacitor $C_o$. However, the driving signal can also follow a parallel path comprising capacitor $C_3$, electrode $24_3$, capacitor $C_2$, electrode $22_1$ and capacitor $C_1$. Thus, any change in the capacitance of capacitors $C_1$, $C_2$ or $C_3$ affects the measurement that is obtained on the electrode $24_2$. Similarly, since the driving signal can follow other parallel paths formed by other sets of surrounding capacitors, changes in their capacitance will also affect the measured signal.

In accordance with the present invention, the effects of the surrounding capacitor on the measured signal is minimized by applying a feedback signal to all of the driving electrodes other than the one associated with the row of interest. This feedback signal is obtained from the output signal of the amplifier 28. In effect, the feedback signal places all of the non-driven electrodes 22 at substantially the same potential as the sensed electrode 24. Referring to FIG. 3, if the electrodes $22_1$ and $22_3$ are at the same potential as the sensed electrode $24_2$, no current will flow through the capacitors $C_1$ and $C_5$. Accordingly, the measured signal will be isolated from the effects of changes in the surrounding electrodes.

Figure 4:
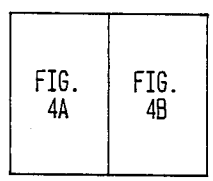
FIG. 4 is a schematic and block diagram of the demultiplexing circuit for supplying the driving signal to the arrays of the pad.
Figure 4A:
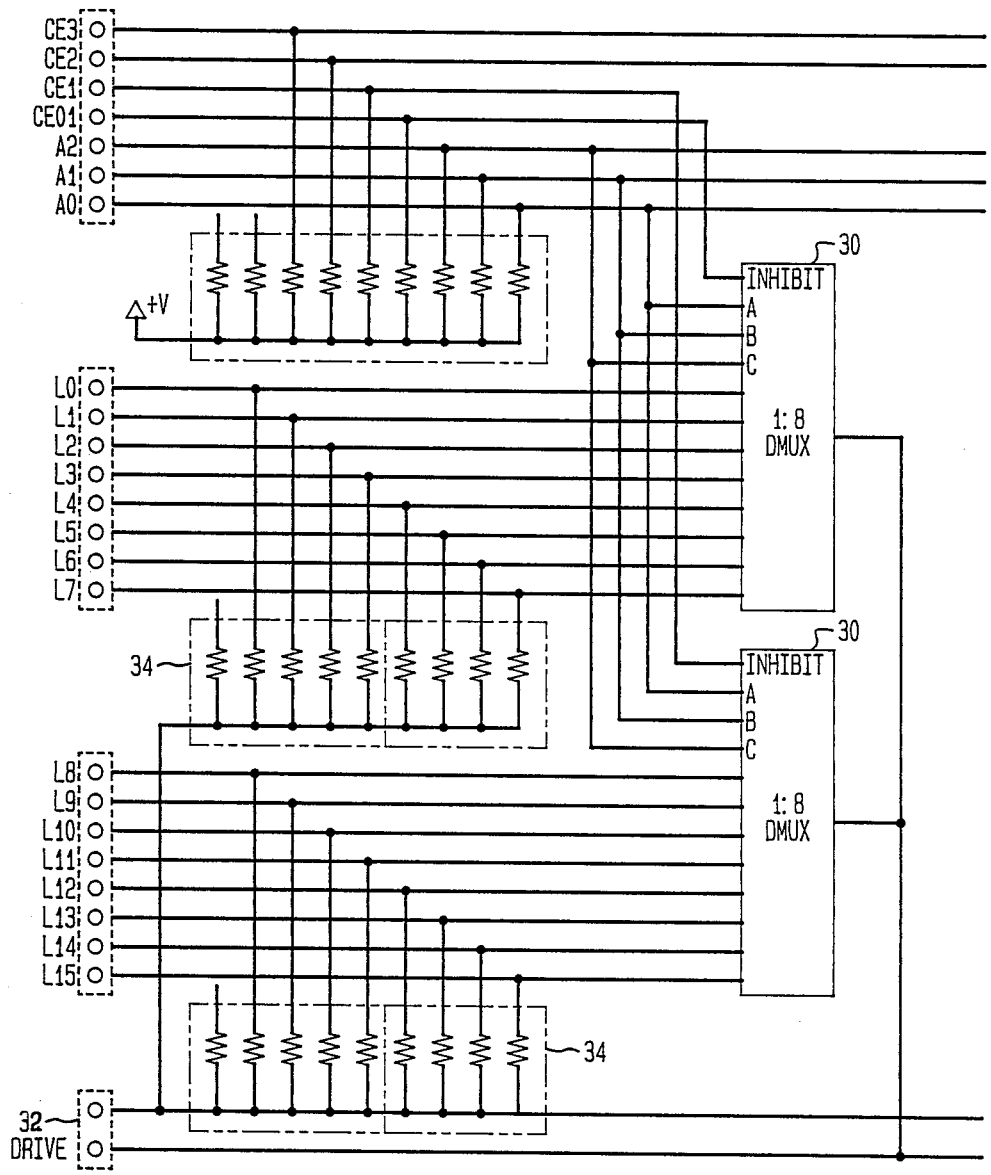
Figure 4B:
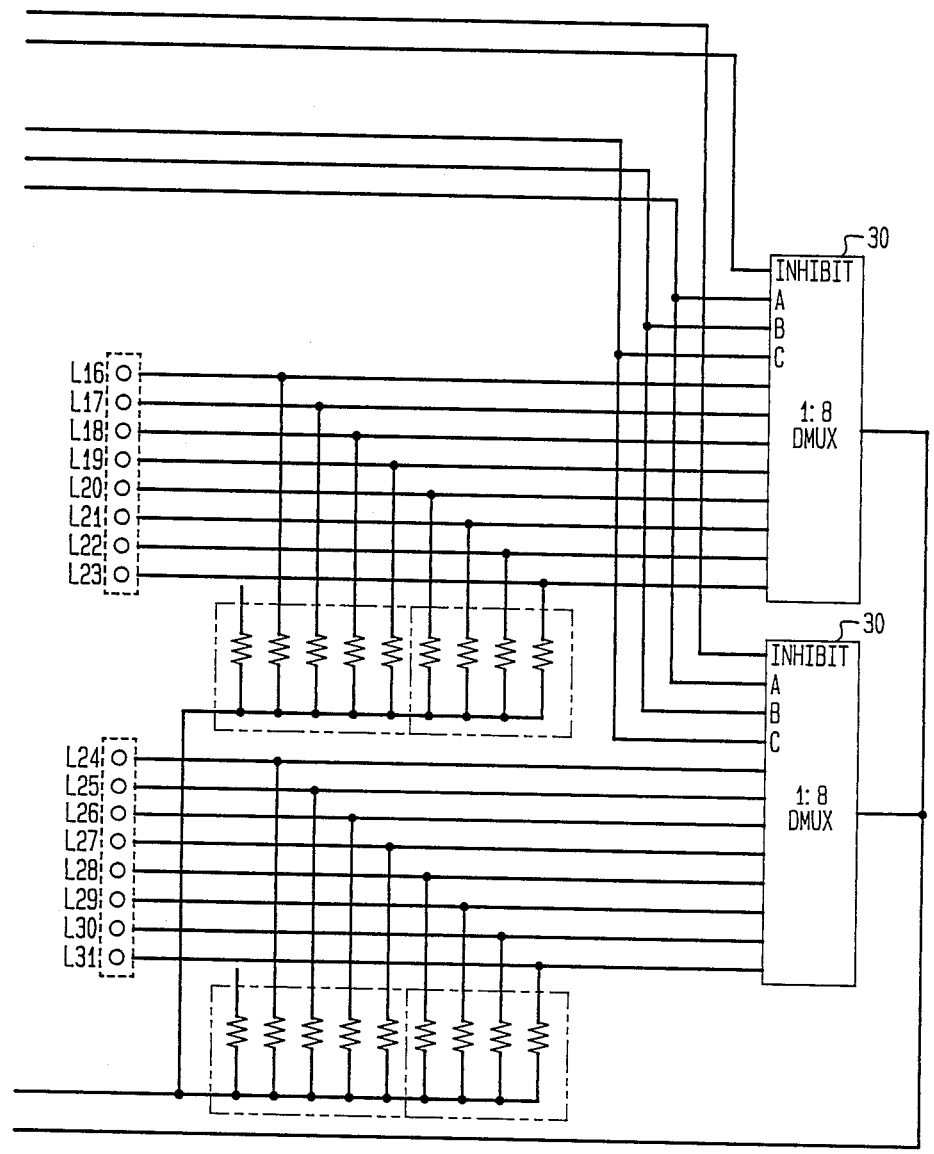

A circuit for implementing this principle is illustrated in FIG. 4. This circuit is contained within the interface unit 14. The illustrated embodiment pertains to a pad which might be of a suitable size for use on a full-sized matress. Such a pad can have 32 electrodes in the driving array and 64 electrodes in the sensing array to form a matrix of 2048 measuring points. The driving electrodes are respectively labelled L0–L31 in FIG. 4. The electrodes are grouped into four sets of eight electrodes each, and each set is respectively connected to the eight output lines of a 1:8 demultiplexer (DMUX) 30. To select one of the drive lines, the particular DMUX to which that line is connected is activated by means of a chip enable signal CE0–CE3. Address signals A0–A2 identify the particular one of the eight output lines of the DMUX that is to be driven. In response to these signals the activated DMUX connects an input driving voltage DRIVE to the identified line. For example, the driving signal can be an 8-volt A.C. signal having a frequency of about 20 KHz.

Each of the drive lines is connected to a feedback terminal 32 by means of an isolation resistor 34. The feedback signal that is applied to the terminal 32 is the output signal from the amplifier 28. The resistors 34 function to isolate the driven electrode from the feedback signal so that it will be at the proper voltage. Preferably, the resistors have a value of around 10K ohms each to provide this function. If their resistance is too low, e.g., 100 ohms, the driving signal will be shorted and the output will be attenuated. On the other hand, if the resistance is too large, e.g., 500K ohms, a phase shift will be introduced in the feedback signal and imperfect error cancellation will occur.

Figure 5:
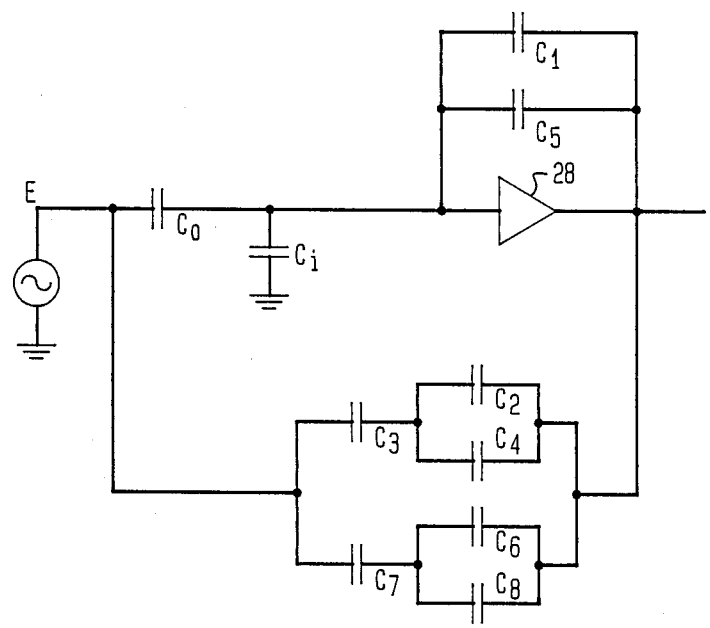
FIG. 5 is a schematic diagram of the equivalent feedback circuit.

The equivalent circuit that is formed when the feedback signal is applied in this manner is shown in FIG. 5. The capacitors $C_2$–$C_4$ and $C_6$–$C_8$, which are not connected to the sensing electrode $24_2$ of interest, merely function to load the generator and do not affect the output signal. However, the capacitors that are connected to the sensed electrode provide a feedback path which could introduce an error into output signal. This feedback path has a resultant capacitance $C_r$, which is the sum of the capacitances connected to the sensing electrode, in this case $C_1 + C_5$. As long as $(1-A)C_r$ is much less than the sum of $C_o$ and $C_i$, the error that is introduced approaches $$\frac{(1-A)C_r}{C_o + C_i}$$

where A is the gain of the amplifier 28. Thus, in order to minimize the error, the amplifier 28 should have a gain that is as close to unity as possible.

To provide an additional level of isolation, the feedback signal can also be applied to each of the sensing electrodes 24 in a similar manner. Otherwise, these electrodes can be left in an electrically floating state.

In operation, the computer sends control signals to the interface unit to sequentially scan each of the measuring nodes. This scanning is carried out through the coordinated addressing of the driving electrode DMUX 30 and a similar multiplexer (not shown) connected to the sensing electrode, as disclosed for example in U.S. Pat. No. 4,134,063. The computer calculates the absolute pressure at each measured mode from the sensed signals in accordance with the relationship defined previously.

The screen of the display monitor 16 is divided into a matrix of cells which correspond to the nodes of the pad. The range of measured pressures can be divided into units that are correlated with individual colors in a color spectrum. The pressure that is measured at each node can thus cause a particular color to be displayed within its associated cell on the screen to provide an easily readable map of pressure distribution in which pressure gradients are indicated by a change in color from one cell to the next As a further feature, the weight of the patient can be determined and indicated on the display by summing the pressure that is measured at each node.

Figure 6:
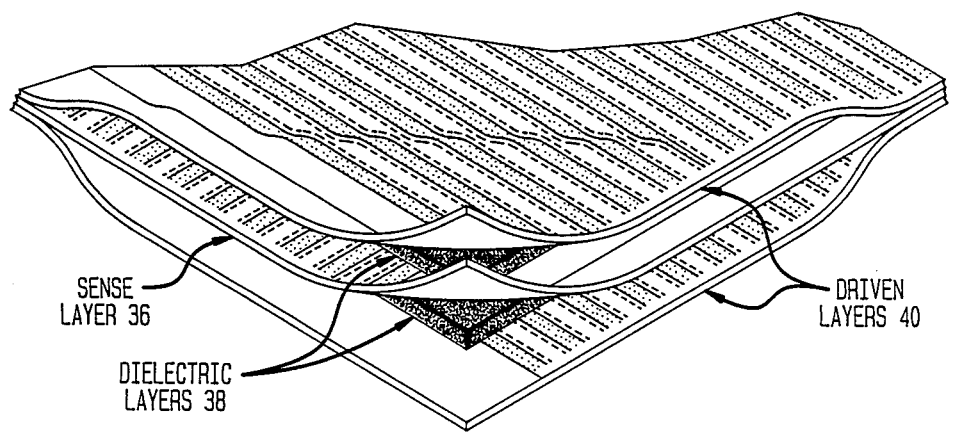
FIG. 6 is a perspective view of a preferred embodiment of the pad.
Figure 7:
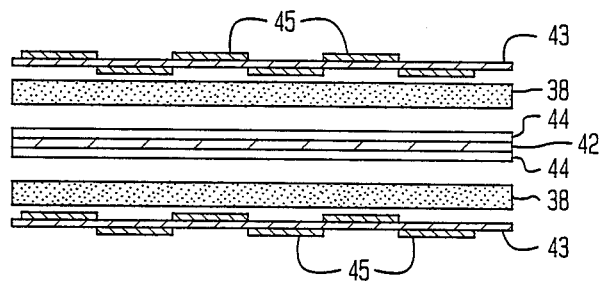
FIG. 7 is a cross-sectional side view of the pad of FIG. 6.

A preferred form of construction for the pad 10 is illustrated in FIGS. 6 and 7. This pad essentially comprises a symmetric integration of two pads of the general type depicted in FIG. 2. A central sensing electrode layer 36 has insulating foam layers 38 disposed on both sides of it. Driving electrode layers 40 are located on the exterior of each of the foam layers. Each electrode layer 36, 40 is comprised of a support material 42, 43, preferably a non-conductive fabric, that has conductive linear electrodes 44, 45 attached to it. Each electrode preferably comprises a strip of conductive fabric, e.g. a nylon that is bonded with a metal such as silver. As best illustrated in FIG. 7, the conductive electrode strips are arranged on alternate sides of the fabric. This arrangement inhibits adjacent electrodes in an array from being shorted due to small wrinkles in the fabric.

The electrodes in the two outer driving layers are aligned with one another, and each pair of aligned electrodes are electrically connected in common with one another. Accordingly, each measuring node is defined by the area of the intersection of a sensing electrode 44 with an aligned pair of driving electrodes 45. This arrangement provides a number of advantages. For example, the capacitance at each node comprises the sum of two capacitors connected in parallel, i.e. one capacitor formed between the sensing electrode layer 36 and the upper driving electrode layer and another capacitor formed between the sensing layer and the lower driving electrode layer. Thus, the signal that is measured is effectively doubled over that which is obtained with a pad having a single insulating layer, and hence easier to read. If the two electrodes in the upper and lower driving layers are not perfectly aligned, the measured signal will not be adversely affected. Rather, any misalignment will merely result in a loss of spatial resolution of the area of the node.

As another advantage, the driving electrode layers that are symmetrically disposed on opposite sides of the sensing layer form electrostatic planes which shield the sensing electrodes from both the patient and the mattress. Thus the measured signal is less likely to be disturbed by outside influences.

To maintain symmetry and ensure that each capacitive node has the same construction, the over and under relationship of the upper and lower driving electrodes is preserved relative to one another. Referring to FIG. 7, it can be seen that if an upper driving electrode 45 is disposed on the exterior side of its support 43, the corresponding lower electrode is located on the interior side of its support, and vice versa. Thus, each pair of parallel connected capacitors at a node will have one capacitor which includes the support fabric 43 between the driving and sensing electrode, and another capacitor which does not include the fabric. To the extent the support fabric has an influence on the capacitance of a node, that effect will be the same for all nodes.

The material that is selected for the dielectric layers 38 should have as little hysteresis as possible in its stress-strain characteristics over the pressure range of interest. If the hysteresis is too large, a patient could pre-load the pad as he gets on the mattress, and hence provide erroneous readings In addition, the material should exhibit negligible creep and have no "memory", i.e. acquire no permanent compression under prolonged loading conditions. If a synthetic foam is used as the dielectric material, a charcoal filled foam provides good results. One example of a suitable charcoal-filled foam is Type SBR foam manufactured by Ludlow.

An even more ideal material in this regard is air, since it exhibits no hysteresis. In the implementation of the invention, individual pockets of air can be confined between two sheets of plastic that are bonded to one another in a matrix pattern, as in FIG. 8. A dielectric layer of this type would have an appearance similar to the "bubble pack" type of material that is used to protect fragile items during packing and shipping. Each pocket of air would define one measuring node, and the electrodes can be easily deposited on the plastic confining layers.

From the foregoing it will be appreciated that the present invention provides a capacitance measuring system that enables the distribution of pressure over a surface to be quantitatively measured and displayed. As noted previously, the information that is provided by the system is useful in the design of sleep surfaces and other furniture, and possibly even clothing. In addition to providing design information, the measuring system can be used in other applications. For example, it can be used to monitor apnea or to detect the exit of a patient from a bed. It might even be used as part of a dynamic feedback system in which the contour of a bed is automatically adjusted in response to movements of the patient to accommodate various reclining positions.

It will therefore be appreciated by those of ordinary skill in the art that the present invention can be embodied in other specific forms without departing from the spirit or essential characteristics thereof. The presently disclosed embodiment is considered in all respects to be illustrative and not restrictive. The scope of the invention is indicated by the appended claims rather than the foregoing description, and all changes that come within the meaning and range of equivalents thereof are intended to be embraced therein.

We claim:

1. A system for monitoring the distribution of forces on a surface, comprising:
   a pad having first and second sheets of compressible insulating material, a first array of linear electrodes disposed between said sheets of insulating material, a second array of linear electrodes disposed on a side of said first sheet of insulating material that is opposite said first array of electrodes and being oriented in a direction other than the direction of the electrodes of said first array to thereby form a matrix of nodes each of which is located at an intersection of an electrode of said first array with an electrode of said second array and which has a capacitance that varies in accordance with compression of said first sheet of said intersection, and a third array of linear electrodes disposed on a side of said second sheet of insulating material that is opposite said first array of electrodes, the electrodes in said third array being oriented parallel to and in alignment with the electrodes of said first array, wherein each array of linear electrodes comprises conductive strips disposed on a substrate, and wherein the conductive strips of at least said first and third arrays are disposed on opposite sides of the substrate in an alternating fashion;
   means for sequentially selecting each electrode of said second and third arrays in correspondence and applying an electrical driving signal to the selected electrodes;
   means for sequentially selecting each electrode of said first array and sensing the electrical potential of the selected electrode of said first array to thereby measure the capacitance of the node at the intersection of the selected electrodes;
   means for providing a signal related to the measured capacitance at each node in the matrix to thereby indicate the distribution of forces on the surface of said pad; and
   means for applying a feedback potential related to said sensed potential to each of the non-selected electrodes of said second and third arrays to thereby isolate the sensed potential from the effects of changes in capacitance of nodes other than said node whose capacitance is being measured.

2. The system of claim 1 further including means for displaying the distribution of forces on said pad in the form of a matrix of cells with each cell depicting the relative capacitance of an associated node on said pad.

3. The system of claim 2 wherein the capacitances of said nodes are in a range which is associated with a spectrum of colors and pressure gradients are represented on said display means by a change in color from one cell to another.

4. The system of claim 1 further including means for determining absolute pressure on the pad at each node thereof in response to the measured capacitance of the node.

5. The system of claim 4 further including means for summing the pressures at all of the nodes to thereby determine the weight of an object on the pad.

6. The system of claim 1 wherein said feedback means includes an amplifier which receives the sensed potential as an input signal and produces said feedback potential as an output signal, said amplifier having a gain which is approximately one.

7. The system of claim 1 wherein said feedback means also applies the feedback potential to each to of the non-selected electrodes of said first array.

8. The system of claim 1 wherein each aligned pair of strips in the first and third electrodes are disposed on the same side of their respective substrates so that, at each node, one of the strips of the pair is disposed on the side of its substrate which is away from said second array and the other strip of the pair is disposed on the side of its substrate which is closest to said second array.

9. A pad for sensing the distribution of pressure on a surface, comprising:
   first and second sheets of compressible insulating material;
   a first array of linear electrodes interposed between said sheets of material and being oriented in a first direction;
   a second array of linear electrodes comprising conductive strips disposed on opposite sides of a substrate in an alternating fashion and disposed on the side of said first sheet that is opposite said first array and being oriented in a second direction which intersects said first direction;
   a third array of linear electrodes comprising conductive strips disposed on opposite sides of a substrate in an alternating fashion and disposed on the side of said second sheet that is opposite said first array, the electrodes of said third array being parallel to and in substantial alignment with the electrodes of said second array, each electrode in said third array being electrically connected to a corresponding aligned electrode in said second array to thereby effectively form two capacitors connected in parallel at each node formed at the intersection of an electrode in said first array with an aligned pair of electrodes in said second and third arrays.

10. The pad of claim 9 wherein the electrodes of said second and third arrays are oriented perpendicular to the electrodes of said first array.

11. The pad of claim 9 wherein each aligned pair of strips in the second and third electrodes are disposed on the same side of their respective substrates so that, at each node, one of the strips of the pair is disposed on the side of its substrate which is away from said first array and the other strip of the pair is disposed on the side of its substrate which is closest to said first array.

12. The pad of claim 9 wherein said insulating material comprises a foam.

13. The pad of claim 9 wherein each of said sheets of insulating material comprises two layers of material which are joined to one another in a manner which forms enclosed cells of air between them, each cell being associated with one of said nodes.

* * * * *